(12) United States Patent
Levy et al.

(10) Patent No.: US 11,503,985 B2
(45) Date of Patent: Nov. 22, 2022

(54) MEDICAL IMAGING DEVICE WITH A FOLDABLE ELECTRONIC CIRCUIT BOARD

(71) Applicant: 270 SURGICAL LTD., Netanya (IL)

(72) Inventors: Avraham Levy, Kfar Shmaryahu (IL); Golan Salman, Atlit (IL); Amram Aizenfeld, Ramot Menshe (IL); Leonid Krivopisk, Nesher (IL)

(73) Assignee: 270 SURGICAL LTD., Netanya (IL)

( * ) Notice: Subject to any disclaimer, the term of this patent is extended or adjusted under 35 U.S.C. 154(b) by 190 days.

(21) Appl. No.: 16/758,057

(22) PCT Filed: Oct. 17, 2018

(86) PCT No.: PCT/IL2018/051111
§ 371 (c)(1),
(2) Date: Apr. 22, 2020

(87) PCT Pub. No.: WO2019/087178
PCT Pub. Date: May 9, 2019

(65) Prior Publication Data
US 2021/0186311 A1 Jun. 24, 2021

Related U.S. Application Data

(60) Provisional application No. 62/578,546, filed on Oct. 30, 2017.

(51) Int. Cl.
*A61B 1/00* (2006.01)
*A61B 1/06* (2006.01)

(52) U.S. Cl.
CPC ...... *A61B 1/00124* (2013.01); *A61B 1/00114* (2013.01); *A61B 1/00128* (2013.01); *A61B 1/00177* (2013.01); *A61B 1/00181* (2013.01); *A61B 1/0607* (2013.01); *A61B 1/0615* (2013.01); *A61B 1/0684* (2013.01)

(58) Field of Classification Search
CPC ............ A61B 1/00124; A61B 1/00114; A61B 1/00128; A61B 1/00177; A61B 1/00181; A61B 1/0607; A61B 1/0615; A61B 1/0684; A61B 1/0676; A61B 1/051; A61B 2562/166; A61B 2562/227; A61B 2562/228; H04N 2005/2255; G02B 23/2484; H05K 3/0008
See application file for complete search history.

(56) References Cited

U.S. PATENT DOCUMENTS 5,547,455 A * 8/1996 McKenna ................ A61B 1/05
600/113
2013/0271588 A1 10/2013 Kirma et al.
(Continued)

*Primary Examiner* — Aaron B Fairchild
(74) *Attorney, Agent, or Firm* — Soroker Agmon Nordman; Sharone Godesh; Daniel Schatz

(57) ABSTRACT

The subject matter discloses a medical imaging device, comprising a rigid elongated member, a rigid distal member connected to the rigid elongated member, wherein said distal member comprises a front camera and a first side camera and a foldable circuit board located within the distal member, said front camera and said first side camera are connected to foldable arms of the foldable circuit board, wherein said foldable circuit board is designed to be put in a foldable position and inserted into said distal member.

10 Claims, 18 Drawing Sheets

(56) References Cited

U.S. PATENT DOCUMENTS

| | | | |
|---|---|---|---|
| 2014/0364691 A1* | 12/2014 | Krivopisk | A61B 1/05 600/109 |
| 2015/0119638 A1* | 4/2015 | Yu | A61B 1/018 600/102 |
| 2016/0015258 A1* | 1/2016 | Levin | A61B 1/05 600/109 |

* cited by examiner

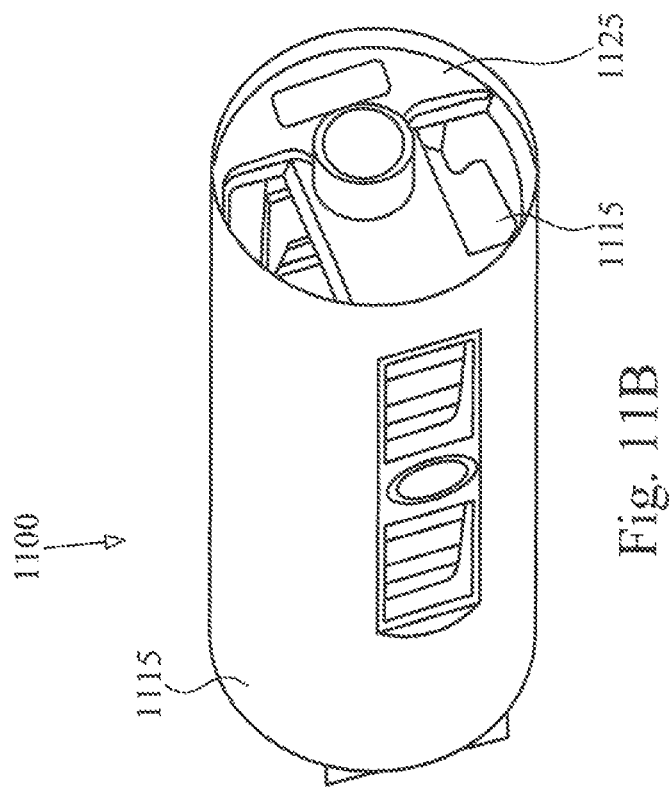
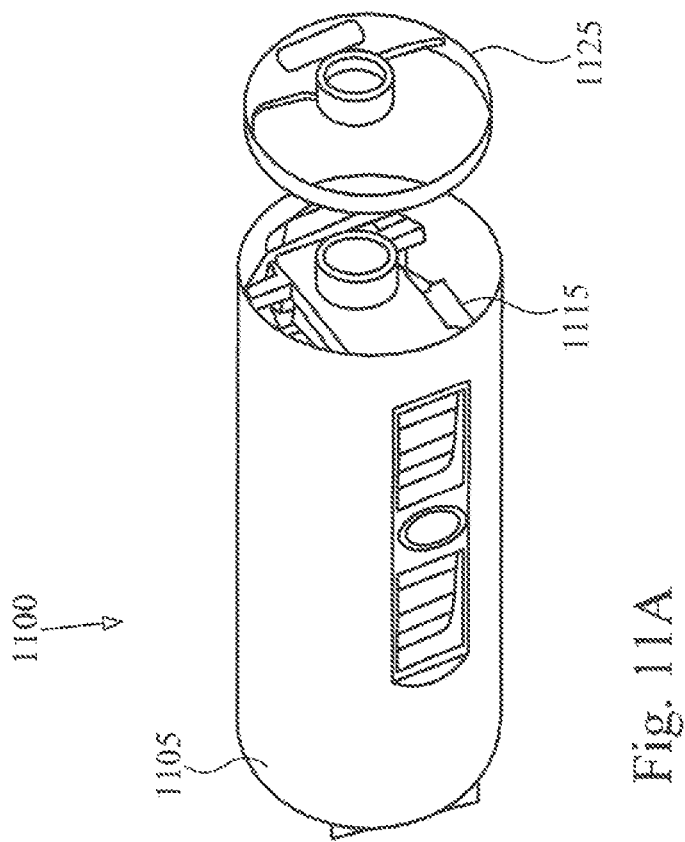
Fig. 11B
Fig. 11A

MEDICAL IMAGING DEVICE WITH A FOLDABLE ELECTRONIC CIRCUIT BOARD

FIELD OF THE INVENTION

The present invention relates generally to the field of medical instruments designed to capture images from inside a lumen.

BACKGROUND OF THE INVENTION

A laparoscope and endoscope devices utilized to perform operations in the internal organs of the body through small entrances in human body. In multiple cases, such operations are required the aid of a camera. Furthermore, in some cases, procedures which involve inspection of a region inside confined area or a specific body cavity or organ, may be required to involve more than one camera. As of today, there are multiple different types of endoscopes and laparoscope, depending on the area/lumen in which the device is used and the procedure's type. As a result of that, to enable the required field of view during the medical procedure the scope has to be maneuvered to region of interest constantly.

A standard laparoscope is likely to be assembled in an elongated tubular member in which the cameras are located, as well as all the electrical circuitry. In most cases, the flexible endoscopes are inserted into the patient's body via the body's natural orifices, while the rigid scopes are inserted via small incision, about 11 millimetres or less, made in the body. On one hand, the elongated tubular member may be narrow to enable maneuvering it within the small incision, in easy and comfortable manner. On the other hand, the elongated tubular member may be required to comprise optical and other components needed for the operation of the rigid scope.

There is therefore a need in the art for rigid endoscopes, such as laparoscopes, that provide a wider field of view and also enable efficient packing of all necessary elements in the tip section, while maintaining their functionality. Thus, in cases more than one camera and the other internal components of the laparoscope are condensed into one elongated and narrow member, the assembling of the circuitry and the optical gear may be complex due to physical constraints of the tubular member and the elementary requirement to keep the lenses and the other optical or/and electrical components functioning for long time without any damage.

SUMMARY OF THE INVENTION

The subject matter disclosed in the present invention discloses a medical imaging device comprising at least two cameras. Said medical imaging device comprises an elongated and narrow distal tip connected to a rigid elongated shaft member, wherein the distal member can comprise a front camera and a first side camera. The distal tip can comprise a foldable circuit board which can be positioned in a folded position and then inserted into the elongated and narrow distal tip. The foldable circuit board may comprise at least two foldable arms which can be configured to carry a front camera and at least one side camera.

In possible embodiments of the present invention, the foldable circuit board may comprise one front camera located on a front foldable arm, and one side camera located on a first side foldable arm. In some cases, second side camera may be connected to the foldable circuit board. The second side camera may be located on the second side foldable arm. In some cases, some of the side cameras may be located on the lateral surfaces of the foldable circuit board. For example, in some cases, the first side camera may be located on a first lateral surface of the foldable circuit board. In some other cases, the second side camera may be located on a second lateral surface of the foldable circuit board. In some cases, the foldable circuit board may also comprise a main rigid section, wherein the three foldable arms may extend from the main rigid section. The foldable arms can also be positioned in an open position in which the three foldable arms are substantially parallel to the surface of the main rigid section and a folded position in which the three foldable arms form an angle versus the surface of the main rigid section.

In some embodiments of the present invention, the foldable arm associated with the first side camera and the foldable arm associated with the second side camera overlap on an axis parallel to the longitudinal axis of the rigid distal member.

In some cases, wherein the foldable circuit board is in a folded position, the foldable arms may be tilted upwardly such that the foldable circuit board may be inserted into a narrow distal tip. In some cases, the distal tip may also comprise a supporting cage designed to be mounted onto said foldable circuit board. Said supporting cage may hold and secure the foldable circuit board and the internal components of said foldable circuit board. In some cases, the supporting case may comprise a longitudinal bar having multiple apertures configured to secure the cameras and illumination modules.

In some embodiments, the disclosed subject matter may comprise two side cameras, a first side camera and a second side camera. The second side camera may be connected on the folded arms situated at the lateral surface of the foldable circuit board and the first side camera may be connected on the folded arms situated at the other side of lateral surface such that the first side camera and second side camera may be pointing at directions essentially opposing to one another. The front camera may be situated on a foldable arm located at the front surface of the foldable circuit board.

The distal tip of the medical imaging device may also comprise a front illumination unit for illuminating the area captured by the front camera a second lateral illumination unit for illuminating the area captured by the second side camera, and a first lateral illumination unit for illuminating the area captured by the first side camera. In some cases, the front illumination unit may comprise four illumination modules.

In some cases, the distal tip may comprise a front optical window located at the front of said distal tip, and in some cases, the distal tip may also comprise at least one side optical window located at the lateral surface of said distal tip. In some cases, the side optical windows and the front optical window may be configured to allow access to the illumination modules located in the distal tip. For example, a person can easily dissolve the glue around the side optical windows to directly reach LEDs and replace if required. In some cases, the distal tip may also comprise a front round frame for supporting and securing front camera.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 11A-11B show a distal tip of a medical imaging device with a multi camera rigid cover, a front camera and a front round frame, according to the disclosed subject matter;

DETAILED DESCRIPTION OF THE INVENTION

The present subject matter discloses a medical imaging device comprising two or three cameras designed to aid medical procedures such as inspection or surgery procedures in the abdomen or pelvis through small incisions. In some cases, such a medical imaging device can be utilized in laparoscopy wherein the medical imaging device can be put through an incision in the body in order to perform medical procedures at the internal organs. In some embodiments of the disclosed subject matter the medical imaging device disclosed herein can comprise two outer section members directly connected. The two outer section members may be an elongated rigid shaft tube and a distal tip cover. The distal tip cover may cover a distal tip, wherein the distal tip can comprise the optical gear required for the medical procedures, and in some cases, be mounted directly on the rigid shaft. In some embodiments, the optical gear located in the distal tip can comprise sensors, lenses and light sources required for the camera functioning. In another embodiment, the medical imaging device disclosed herein can comprise one outer rigid section, wherein the distal part of the outer rigid section may comprise the distal tip.

In some embodiments of the disclosed subject matter the distal tip may comprise a distal housing which may hold a foldable circuit board configured to carry one front camera, at least one side camera, and a cage configured to support and hold said foldable electronic circuit board. Said distal housing may also comprise a front illuminator circuit board, and at least one side illuminator circuit board.

Figure 1:
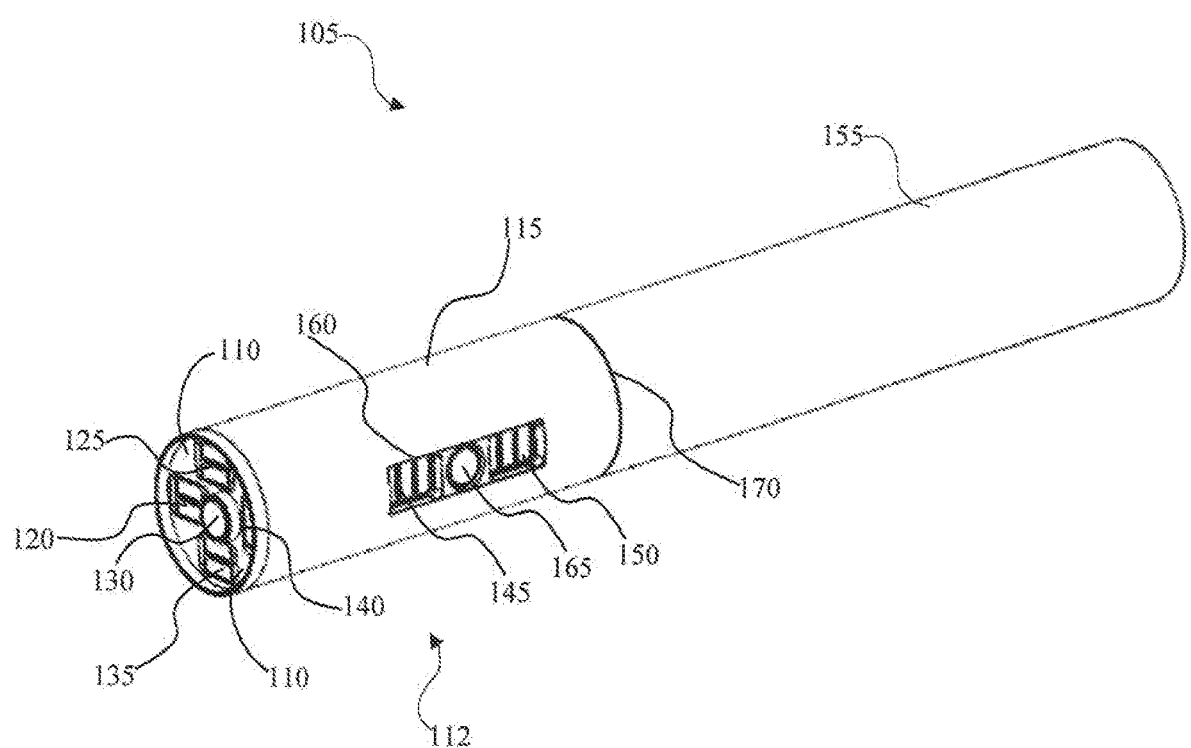
FIG. 1 demonstrates a medical imaging device comprising at least one camera, according to exemplary embodiments of the disclosed subject matter.

FIG. 1 demonstrates a medical imaging device comprising at least one camera, according to exemplary embodiments of the disclosed subject matter. FIG. 1 shows a medical imaging device 105 comprising a rigid elongated shaft 155 designed to be directly connected to a distal tip cover 115, wherein distal tip cover 115 may cover the optical gear (not shown) of the distal tip 112. In such cases, the seamline 170 outlines the connection line between the elongated rigid shaft 155 and the distal tip cover 115. In some cases, the elongated rigid shaft 155 and the distal tip cover 115 may be connected by an adhesive material that seals the connection at the seamline 170. In some other cases, the elongated rigid shaft 155 and the distal tip cover 115 may be connected by soldering. In possible embodiments of the disclosed subject matter, the elongated rigid shaft 155 and the distal tip cover 115 may be connected by a screwing mechanism which fastens the elongated rigid shaft 155 and the distal tip cover 115 together. In yet another embodiment (not shown), the elongated rigid shaft 155 extends along the length of medical imaging device 105 covering a distal tip 112.

The distal tip 112 may function as a multi-camera section member designed to house at least one camera. In some cases, the cameras of the distal tip 112 may be located in the front at the planar surface 110. Additional cameras may be located at the lateral round surface of the distal tip cover 115. The distal tip cover 115 may also comprise an aperture 160 shaped to house a second side camera 165 and provide the opening required for the field of view of the second side camera 165. In some cases, the aperture 160 may be covered by a transparent layer, such as glass or plastic, to isolate the side camera 165 from the patient's tissue. In some other cases, aperture 160 may be covered by an optical window or more than one optical window.

In some embodiments, the distal tip 112 may comprise a first side camera (not shown) located at the opposite side of the distal tip 112. The aperture 160 also enables emission of light from side illuminators 150, and 145 which provide the light source of the side camera 165. In some cases, the light may be emitted by dedicated section illuminators such as light-emitting diodes, also known as LED.

The distal tip 112 may also comprise a front camera 130 situated at the center of a planar surface 110 which can house the front camera 130 and provide the opening required for the field of view of the front camera 130. The planar surface 110 also comprise front illuminators 120, 125, 135, and 140 which provide the required source of light for front camera 130. In other possible embodiments, the number and location of front illuminators may vary for example, less than 4 set of illuminators or more wherein each set of illuminators has 1, 2, 3, 4 or more LED and may emit the same light spectrum or different light spectrum.

Figure 2:
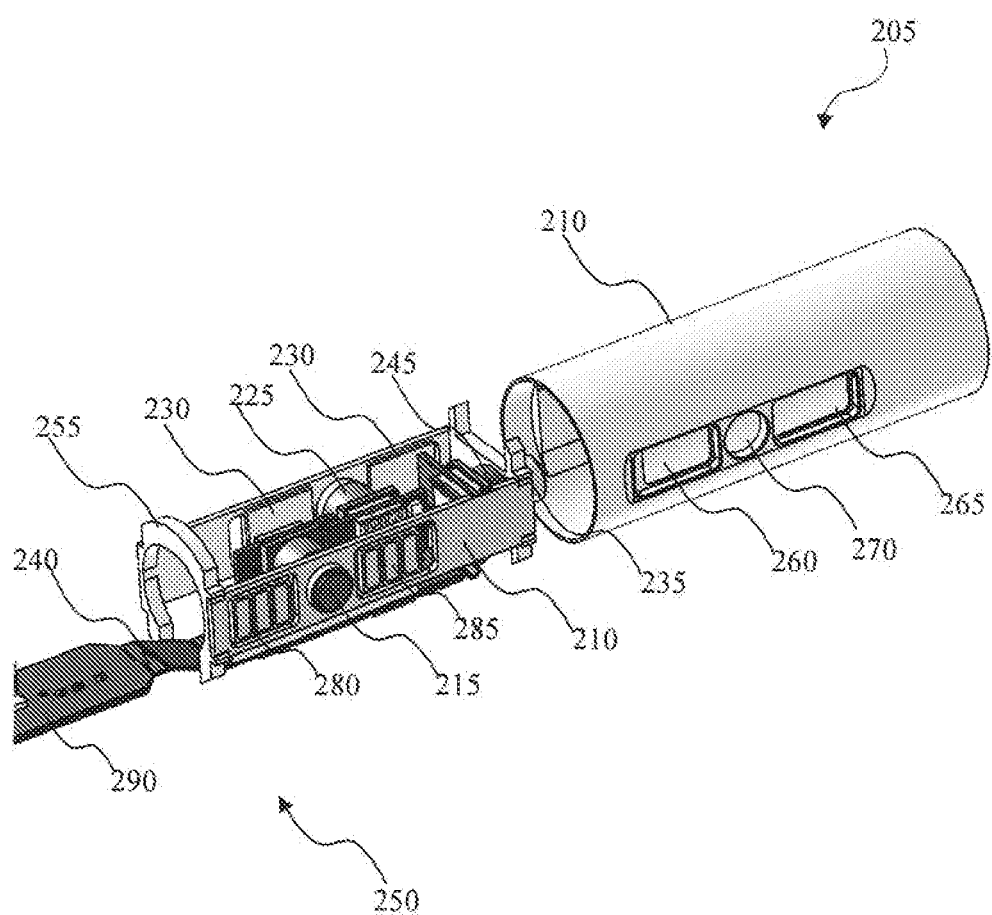
FIG. 2 demonstrates a distal tip comprising a distal housing with a foldable circuit board and a cage designed to fasten thereof, according to exemplary embodiments of the disclosed subject matter.

In some other cases, a portion of the illuminators 150, 145, 120, 125, 135, and 140 which provide the required source of light of the medical imaging device 105 may be at different colors at the visible light. For example, the light source of the medical imaging device 105, may comprise LED's emitting a white light LED and or other colors such as blue, red, yellow, green, or any combination thereof. In some cases, the light emitted by the LED's may be at the spectrum of the non-visible light. For example, a source light can provide a light at the infrared spectrum, ultra-violate, x-ray, and the like FIG. 2 demonstrates a distal tip comprising a distal housing with a foldable circuit board and a cage designed to fasten thereof, according to exemplary embodiments of the disclosed subject matter. FIG. 2 shows a distal part of a medical imaging device 205 with a distal housing 250 which can be threaded into a multi camera rigid cover (distal tip cover) 210 of rigid scope 205. In this embodiment, the multi camera rigid cover 210 comprises a first side hole 270 shaped to house a second side camera and provide the opening required for the camera to capture the field of view. The multi camera rigid cover 210 also comprises second side apertures 260, and 265 located on a longitudinal axis of multi camera rigid cover 210 on both side of hole 270 and shaped to house light sources required for the camera operation as aforementioned. For example, in case the distal housing 250 is threaded into the multi camera rigid cover 210, the first side hole 270 can be fully overlapped with a second side camera 215. In this case, the second side apertures 260, and 265 can also be fully overlapped with second side illuminators 280, and 285 and thereby provide the required opening for the illumination of the second side camera 215. In some cases, the multi camera rigid cover 210 may comprise a second side hole and second side apertures (not shown) at the opposite side of lateral surface of the multi camera rigid cover 210 for housing the first side camera 225 and first side illuminators (not shown). In such cases, the first side camera 225 and second side camera 215 may be pointing at directions essentially opposing to one another.

The distal housing 250 shown in FIG. 2 comprises a foldable circuit board 240 designed to hold the optical gear required for imaging operation of the medical imaging device. For example, the first side camera 225, the second side camera 215 and the front camera 245 can be mounted on the foldable circuit board 240. The structure of the foldable circuit board 240 may allow locating the first side camera 225, the second side camera 215 and the front camera 245 within the multi camera rigid cover 210. The foldable circuit board 240 may also associate with side illuminator circuit boards such as first side illuminator circuit board 230, and second side illuminator circuit board (not shown). The first side illuminator circuit board 230 may be adapted for supporting first side illuminators (not shown) wherein the second side illuminator circuit board may be adapted for supporting second side illuminators 280 and 285. Side illuminator circuit boards are configured to provide the electricity and the electrical signals required for the side illuminators to provide the light. In some cases, the side illuminator circuit boards, may be soldered or screwed into the foldable circuit board 240. In some cases, the foldable circuit board 240 may comprise additional circuits and electrical components to convey and control the electrical signals and the electrical power required for the operation of the cameras.

The distal housing 250 also comprises a supporting cage 255 which can be mounted onto the foldable circuit board 240 and function as a chassis which limits the leeway of the foldable circuit board 240. For example, in some cases, once the first side camera 225, the second side camera 215 and the front camera 245 are mounted on the foldable circuit board 240, the supporting cage 255 can be placed onto the foldable circuit board 240 and thereby to prevent the cameras and the other components of the distal housing 250 from moving or changing positions. Once the supporting cage 255 is mounted onto the foldable circuit board 240, the distal housing 250 can be threaded into the multi camera rigid cover 210.

In some cases, the foldable circuit board 240 may comprise rear rigid section 290 which may carry at least some of the conductors and the electronic cables of the foldable circuit board 240. In some cases, the rear rigid section 290 may be elongated and extend from the distal tip such that the rear rigid section 290 may be located at the rigid shaft (not shown) of the medical imaging device 205.

Figure 3A:
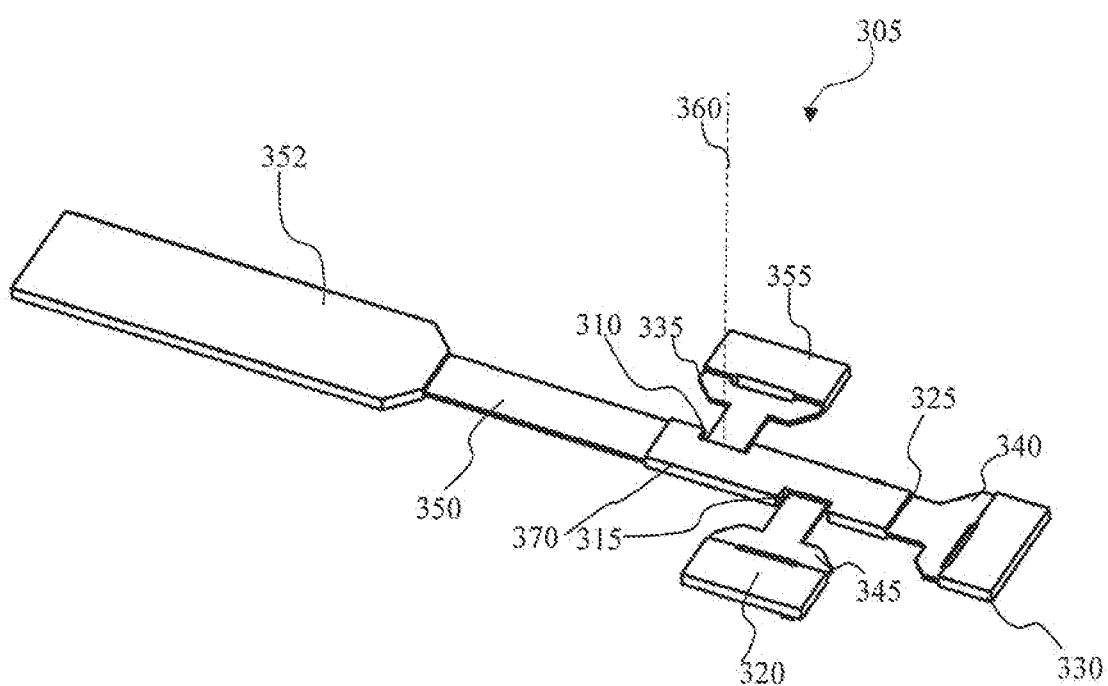
FIG. 3A shows a foldable circuit board in an open position, according to exemplary embodiments of the disclosed subject matter.

FIG. 3A shows a foldable circuit board in an open position, according to exemplary embodiments of the disclosed subject matter. FIG. 3A shows a foldable circuit board 305 stripped-down in an open position. The foldable circuit board 305 comprises a second side/lateral foldable arm 335, a first side/lateral foldable arm 345 and a front foldable arm 340. foldable areas 310, 315 and 325, may connect the foldable arms 335, 345 and 340, respectively and a main rigid section 370 of foldable circuit board 305. FIG. 3A shows the foldable arms 335, 340 and 345 situated downwards, horizontally to the foldable circuit board 305. In some cases, the cameras of the medical imaging device may be placed on the foldable arms at the opposite side of the electronic circuit boards, as explained below.

In possible embodiments of the disclosed subject matter, foldable circuit board 305 and the foldable areas 310, 315 and 325 may be made of typical materials used for making PCB boards are ceramic, polyamides for flexible board, and glass-reinforced epoxy, and the like such, also provide the elastic movement required for the rotations of the foldable arms. In some cases, the foldable area 310, 315 and 325 may comprise hinges which can provide the ability to rotate/bend the foldable arms 335, 340, and 345 upwardly or downwardly. The foldable arms 335, 340, and 345 can be situated horizontally to the main rigid section 370 or, be bended upwardly, essentially vertically to the longitudinal axis of the main rigid section 370. For example, the foldable arms 335 can bend around the foldable area 310 and be positioned in 45 degrees to the vertical axis 360 of foldable circuit board 305. In some cases, the foldable arms 335 can bend further, around the foldable area 310 and be positioned essentially vertically to the main rigid section 370, with zero degrees between the foldable arm 335 and the vertical axis 360. In some cases, some of the foldable arms 335, 340 and 345 may be situated with any angle on the range between the perpendicular and horizontal angles to the foldable circuit board 305.

The foldable circuit board 305 also comprises a second side rigid section 355 attached to the second side foldable arm 335. The second side rigid section 355 may be designed to carry a camera, wherein the camera typically comprises a sensor and a lens assembly and which can be attached on the second side rigid section 355 and is required for the operation of the medical imaging device. Similarly, foldable circuit board 305 also comprises a first side rigid section 320 designed to carry a camera, wherein this camera typically comprises a sensor and a lens assembly which can be attached to the rigid section 320, and a front rigid section 330 designed to carry a front camera, wherein this camera typically comprises a sensor and a lens assembly which can be attached to the front rigid section 330. Said cameras may be attached directly to the rigid sections 320, 330 and 355 by adhesive material, screws, clamping devices, and the like. In some embodiments of the disclosed subject matter, the cameras attached to rigid sections 320, 330 and 355 may also comprise image sensors such as a Charge Coupled Device (CCD) or a Complementary Metal Oxide Semiconductor (CMOS). In some embodiment, front, and each of the side cameras have the same sensors and lens assemblies, yet in anther embodiments, the cameras may be different, such the front camera and each of the side cameras may be the same or different in any one or any combinations of their components or other element related to them (such as optical elements).

In some cases, the foldable arms 335 and 345 may be positioned such that the field of views of the cameras attached to the side rigid sections 355 and 320 may be substantially opposing and perpendicular or almost perpendicular to the field of view of front camera attached to front rigid section 330.

In some embodiments, foldable arms 335 and 345 may be positioned back to back (not shown) in an equal distance from foldable arm 340 along main rigid section 370. In other embodiments, foldable arms 335 and 345 may be positioned in unequal distances from foldable arm 340 along main rigid section 370. Such, second side foldable arm 335 may be positioned in a larger distance from foldable arm 340 along main rigid section 370 compared to first side foldable arm 345 or vice versa.

The foldable circuit board 305 further comprises a rear foldable section 350 situated between main rigid section 370 and a rear rigid section 352. Rear rigid section 352 may carry some of the conductors and the electronic cables of the foldable circuit board 305. In some cases, the rear rigid section 352 may carry all the conductors and the electronic cables of the foldable circuit board 305.

Figure 3B:
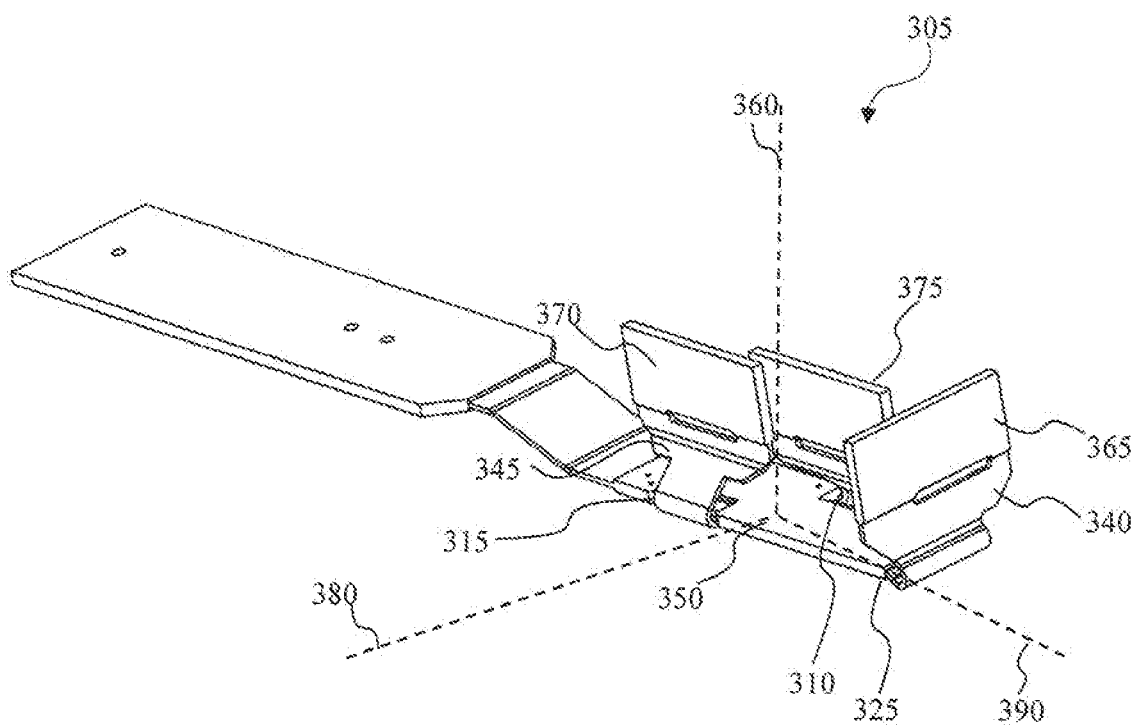
FIG. 3B shows a foldable circuit board with foldable arms pointing upwards, according to FIG. 3A.

FIG. 3B shows a foldable circuit board with foldable arms aiming upwards, according to FIG. 3A. FIG. 3B shows a foldable circuit board 305 stripped-down in a folded position. The foldable circuit board 305 comprises a foldable arm 335, a foldable arm 340 and a foldable arm 345 attached to a main rigid section 370 of foldable circuit board 305. The foldable arms 335, 345, and 340 are attached to the main rigid section 370 by foldable areas 310, 315 and 325, respectively. FIG. 3B shows the foldable arms 335, 340 and 345 situated upwards, essentially vertically to the main rigid section 370. The foldable arm 345 comprises a plain surface 370 designed to comprise the internal components required for the operation of the cameras. Similarly, the foldable arms 335 and 345 may have plain surfaces 375 and 365, respectively, designed to comprise the internal components required for the operation of the cameras. In some cases, the internal components may be such as, circuits, solid state components, conductors, capacitors, diodes, circuit breakers, circuit boards and the like.

In some cases, the foldable arms 335, 340, and 345 may be bended and placed in an open position, wherein the foldable arms 335, 340, and 345 are positioned in parallel to the imaginary plain created by horizontally axes 380, and 390. In some cases, the foldable arms 335, 340, and 345 may be placed in a folded position, wherein the foldable arms 335, 340, and 345 are positioned in parallel to the vertical axis 360. In some other cases, the foldable arms 335, 340, and 345 may be placed in any angle on the range between the vertical axis 360 and the imaginary plain created by the horizontally axes 380, and 390.

Figure 3C:
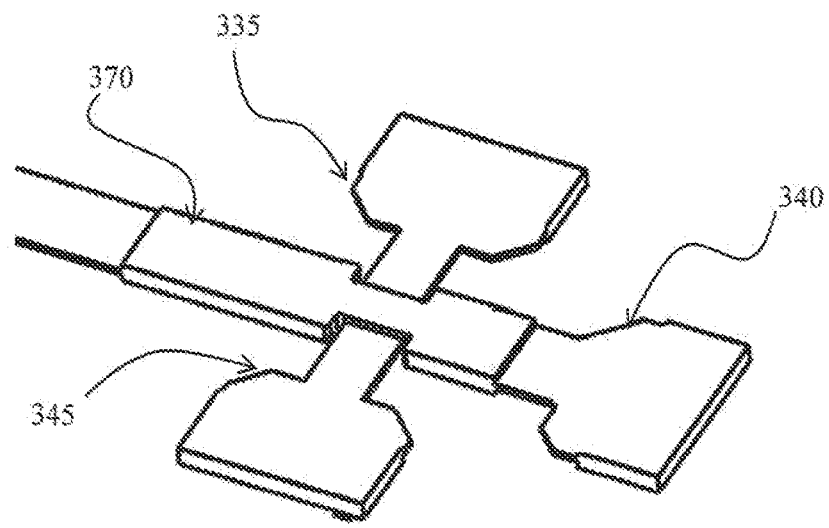
FIG. 3C-3D show a foldable circuit board in an open position and foldable position, respectively, according to other exemplary embodiments of the disclosed subject matter.
Figure 3D:
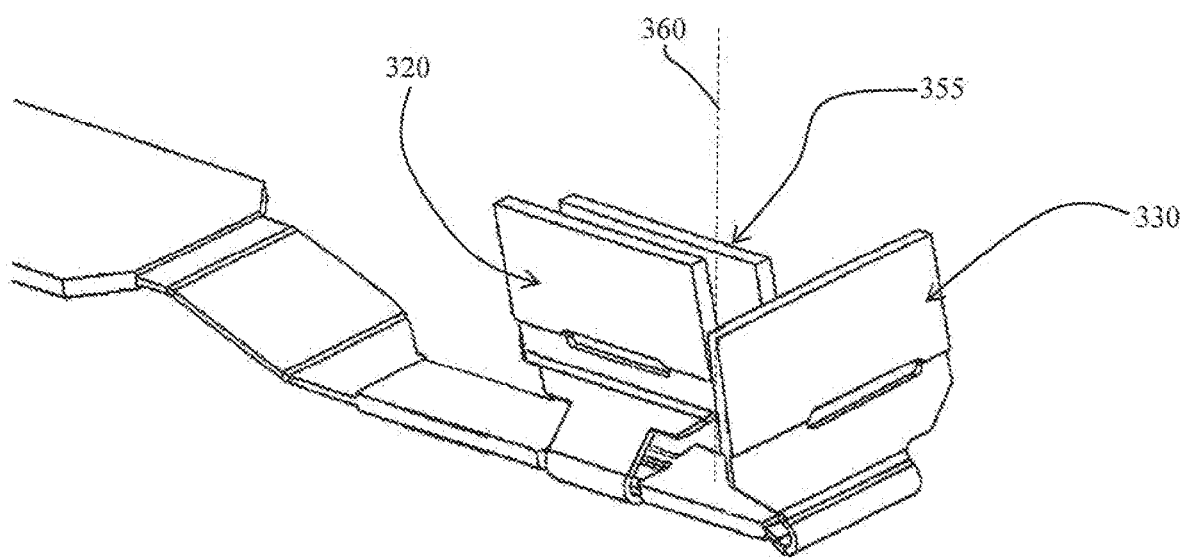

FIG. 3C-3D show possible other embodiments, wherein foldable arms 335 and 345 may be positioned back to back in an equal distance from foldable arm 340 along main rigid section 370. FIG. 3C shows first side foldable arm 345 and second side foldable arm 335 placed in an equal distance from front foldable arm 340, the front and two side foldable arms are depicted in an open position. As described above, foldable arms 335, 340, and 345 have a foldable position parallel to vertical axis 360, as depict in FIG. 3D. Foldable arms 335 and 345 back to back position enables field of views of cameras (not shown) attached to side rigid sections 355 and 320 to be substantially opposing and perpendicular or almost perpendicular to the field of view of front camera (not shown) attached to front rigid section 330.

Figure 4:
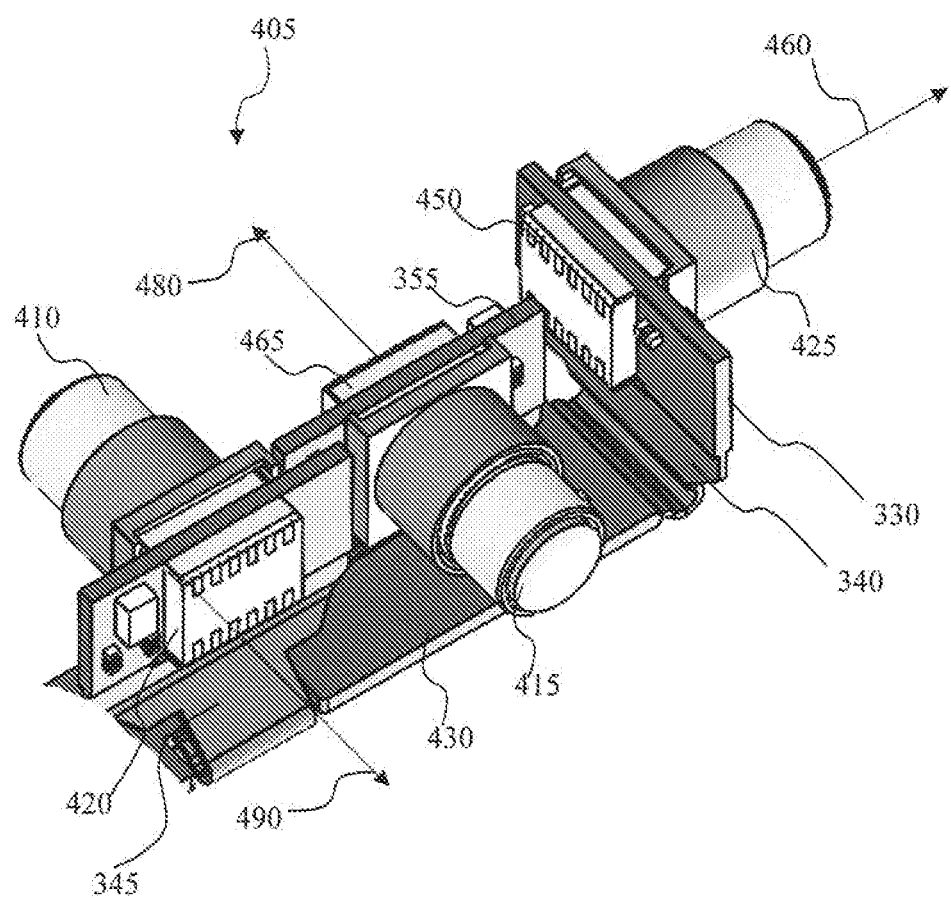
FIG. 4 shows internal components of a foldable circuit board in the folded position of FIG. 3B.

FIG. 4 shows a distal housing with the internal components of a foldable circuit board in a folded position, according to exemplary embodiments of the disclosed subject matter. FIG. 4 shows a distal housing 405 comprises a foldable circuit board 430 comprising the internal components required for the operation of the medical imaging device. The internal components of the foldable circuit board 430 may be configured to be assembled together in a slim and condensed fashion, such that the distal housing 405 can be threaded into a rigid cover of a medical imaging device.

The foldable circuit board 430 comprises a front foldable arm 340 having a front rigid section 330 and adapted to carry a front camera 425, wherein the camera typically comprises a sensor and a lens assembly, attached to the outer surface of the front rigid section 330, and internal components 450 attached to the inner surface of the front rigid section 330. In some cases, the foldable arm 340 may move forward at the direction of arrow 460 in order to situate the foldable arm 340 in an open position, as shown in FIG. 3A.

The foldable circuit board 430 also comprises a second side foldable arm 345 having a second side rigid section 320 and adapted to carry a second side camera 410, wherein the camera typically comprises a sensor and a lens assembly, attached to the inner surface of the second side rigid section 320, and internal components 420, located at a second side of second side rigid section 320. In some cases, the second side foldable arm 345 may move forward at the direction of arrow 490 in order to situate the second side foldable arm 345 in an open position, as shown above.

The foldable circuit board 430 also comprises a first side foldable arm 335 having a first side rigid section 355 and adapted to carry a first side camera 415, wherein the camera typically comprises a sensor and a lens assembly, attached to the outer surface of the first side rigid section 355, and internal components 465, located at the inner side of first side rigid section 355. In some cases, the first side foldable arm 335 may move forward at the direction of arrow 480 in order to situate the first side foldable arm 335 in an open position. In some cases, the second side camera 410 and the first side camera 415 may be situated such that they may be pointing at directions essentially opposing to one another.

Figure 5:
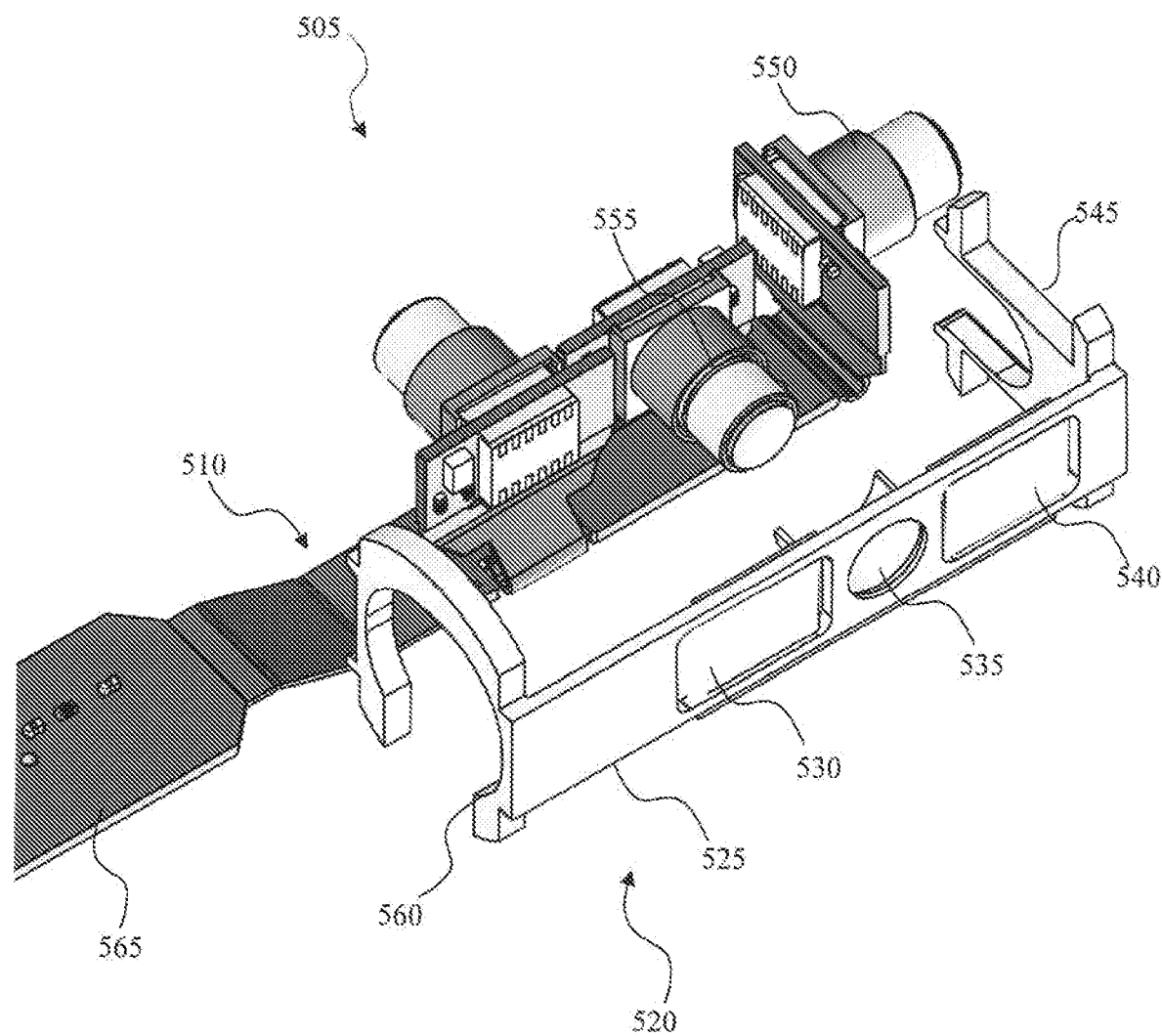
FIG. 5 shows a distal housing comprising a foldable circuit board in a folded position and a first component of a supporting cage designed to fasten thereof, according to exemplary embodiments of the disclosed subject matter.

FIG. 5 shows a distal housing comprising a foldable circuit board in a folded position and a first component of a supporting cage designed to fasten thereof, according to exemplary embodiments of the disclosed subject matter. FIG. 5 shows a distal housing 505 comprising a foldable circuit board 510 and a first component of the supporting cage 520. The first component of the supporting cage 520 may be configured to hold and support the foldable circuit board 510 in a folded position and secure the front camera and the two side cameras as well as the corresponding illuminator boards in place. The first component of the supporting cage 520 comprises a U-shaped closure 560 designed to encompass the foldable circuit board 510 and to support and hold the electronic cables within first component of the supporting cage 520. In some cases, the U-shaped closure 560 may also be mounted on a distal tip (not shown) and thereby limit leeway of the foldable circuit board 510 within the distal tip. The foldable circuit board 510 may comprise a rear rigid section 565 which may carry some of the conductors and the electronic cables of the foldable circuit board 510. In some cases, the rear rigid section 565 may be elongated and extend from the distal tip such that the rear rigid section 565 may be located at the rigid shaft (not shown) of the medical imaging device.

The first component of the supporting cage 520 may also comprise a longitudinal bar 525 designed to stretch along the side foldable arms of the foldable circuit board 510 and in some cases, function as a house for some of the internal components required for the operation of the medical imaging device. The longitudinal bar 525 may comprise a first side camera opening 535 designed to hold and secure the first side camera 555, and first side illumination openings 530 and 540 designed to hold and secure the first side illuminators circuit board required for the operation of the first side camera 555. The longitudinal bar 525 can be attached in one end to the U-shaped closure 560 and at the other end to a U-shaped socket 545 which may be configured to hold and secure the front camera 550.

In some embodiments of the disclosed subject matter, the first component of the supporting cage 520 may be formed as a unitary piece of rigid material, such as brass, stainless steel, aluminum, and the like. The longitudinal bar 525 may be formed to connect between the U-shaped closure 560 and the U-shaped socket 545, and thereby provide the firm structure and the sturdiness required for the first component of the supporting cage 520. In possible embodiments, the longitudinal bar 525 may be soldered to the U-shaped closure 560 and the U-shaped socket 545.

Figure 6:
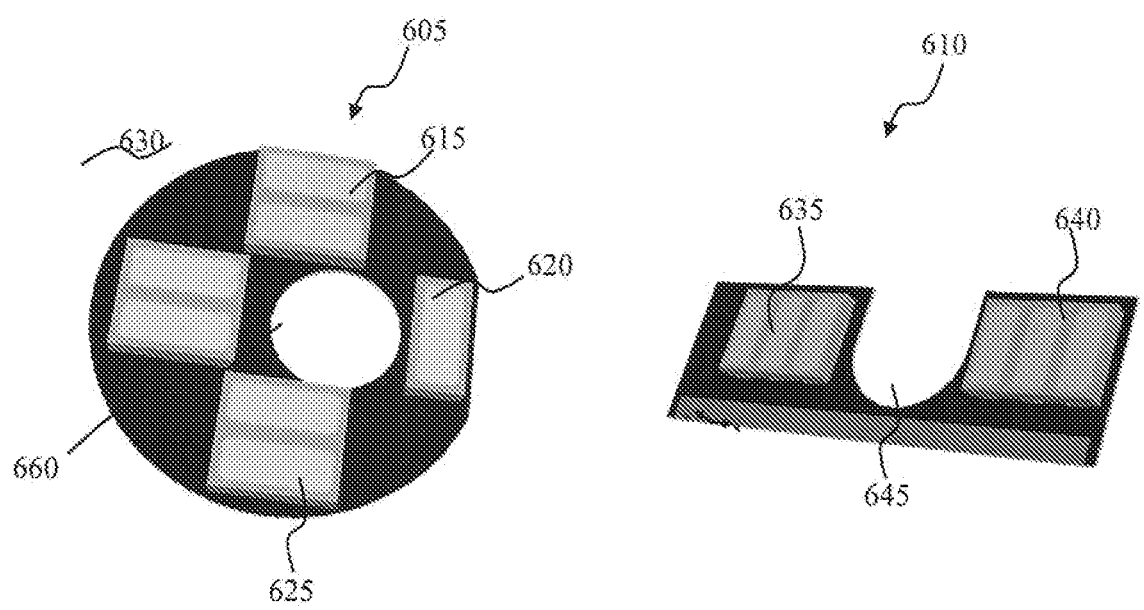
FIG. 6 shows a front illuminator electronic circuit and a side illuminator electronic circuit, designed to provide the light source for the medical imaging device's camera, according to exemplary embodiments of the disclosed subject matter.

FIG. 6 shows a front illuminator electronic circuit and a side illuminator electronic circuit, designed to provide the light source for the medical imaging device's camera, according to exemplary embodiments of the disclosed subject matter. FIG. 6 shows a front illuminator electronic circuit 605 which can hold a set of four front illumination modules, represented as illumination modules, 615, 620, 625, and 630 and secure a front camera (not shown) with an opening 660. In some cases, the front camera opening 660 may not be positioned in the center of the front surface of the medical imaging device. Thus, the front illumination modules 615, 620, 625, and 630 may hold a different number of illuminators. In some embodiments, front illuminator electronic circuit 605 can hold a set of 1, 2, 3, 4, 5 or more front illumination modules.

Optionally, the front camera opening 660 is positioned in the center of the front surface of the medical imaging device. Thus, the front illuminator modules may or may not hold the same number of illuminators.

FIG. 6 also shows a side illuminator electronic circuit 610 designed to support the side illuminators of a medical imaging device. The side illuminator electronic circuit 610 comprises a side illumination module 635 and side illumination module 640 which may hold 1 or more illuminators. In some cases, each module may hold a different number of illuminators. In some embodiments of the disclosed subject matter, the side illuminator electronic circuit 610 may have a U-shaped socket 645 which can contain the side camera. The side illumination modules may be on either side of the side camera.

Figure 7:
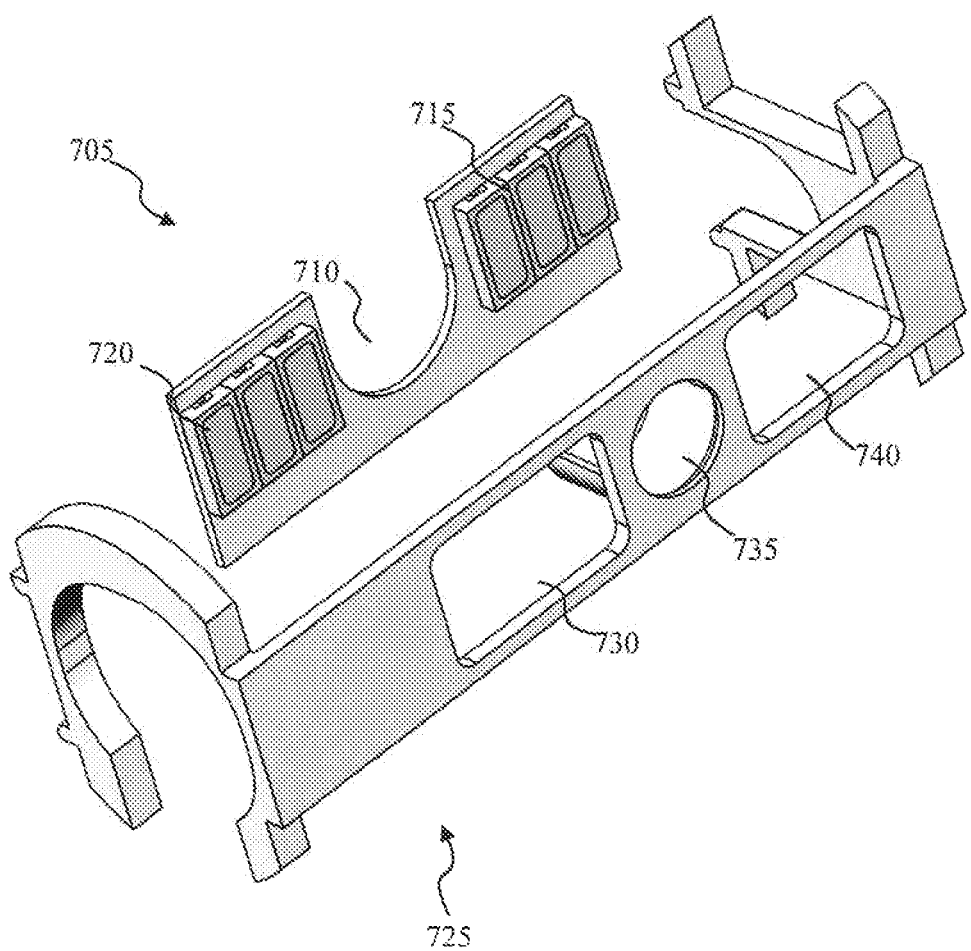
FIG. 7 shows a view of a side illuminator electronic circuit board and a first component of a supporting cage, according to exemplary embodiments of the disclosed subject matter.

FIG. 7 shows a view of a side illuminator electronic circuit board and a first component of a supporting cage, according to exemplary embodiments of the disclosed subject matter. FIG. 7 shows a first component of the supporting cage 725 and a side illuminator electronic circuit 705 board holding a set of two side illumination modules, a side illumination module 720 and a side illumination module 715. Said side illumination modules may hold 1 or more illuminators. In some cases, each module may hold a different number of illuminators. The side illuminator electronic circuit 705 also comprises a U-shaped socket 710 which can be mounted onto the first component of the supporting cage 725, wherein the U-shaped socket 710 encompasses the side camera opening 735. The side illumination modules 715, and 720 can also be mounted onto the first component of the supporting cage 725, wherein the side illumination module 715 can fit into the illuminator opening 740, and wherein the side illumination module 720 can fit into the illuminator opening 730. Thus, the illuminator opening 730, and 740 can hold and secure the side illumination modules 720, and 715, respectively.

Figure 8:
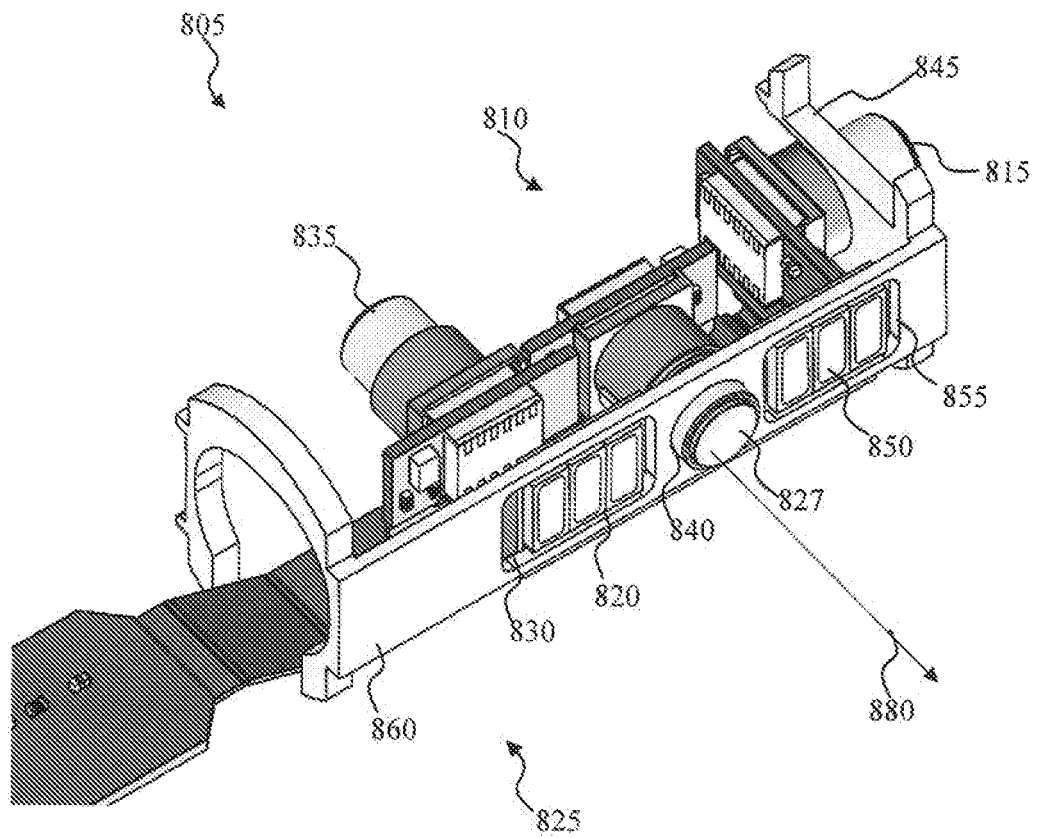
FIG. 8 shows a distal housing comprising a first component of a supporting cage mounted on a foldable circuit board in a folded position, according to the disclosed subject matter.

FIG. 8 shows a distal housing comprising a first component of a supporting cage mounted on a foldable circuit board in a folded position, according to the disclosed subject matter. FIG. 8 shows a distal housing 805 comprising a first component of a supporting cage 825 mounted on a foldable circuit board 810. The first component of a supporting cage 825 may be configured to fasten, secure and hold the foldable circuit board 810 in a folded position. Thus, a front camera 815 can fit into the U-shaped socket 845 of the first component of a supporting cage 825 such that the U-shaped socket 845 can hold and secure the front camera 815. In a similar fashion, a first side camera 827 can be inserted into a side camera opening 840 such that the camera socket 840 can hold and secure the first side camera 827.

The first component of a supporting cage 825 also comprises an illuminator opening 830 and illuminator opening 855, located on the longitudinal bar 860 and designed to hold and secure a side illumination module 820 and a side illumination module 850, respectively. In some cases, the side illumination modules 820, and 850 may be attached to the illuminator opening 830, and 855 by an adhesive material which can maintain the illumination modules 820, and 850 fastened and steady. In some cases, the side illumination modules 820, and 850 may be attached to the illuminator opening 830, and 855 by utilizing other techniques. Said techniques may be such as, tiny screws, fastener clips, tiny sockets, rail shaped slots, and the like. In some embodiments, side illuminator modules 820 and 850 may be attached to first component of a supporting cage 825 in replaceable manner techniques enabling the replace of illuminator module 820 or illuminators module 850 or any illuminator within these modules 820 and 850.

In some embodiments of the disclosed subject matter the first component of a supporting cage 825 may be provided with opposite sides, wherein the longitudinal bar 860 can extend along the foldable circuit board 810 at the side of the second side camera 835. Thus, the second side camera 835 may be inserted into the camera opening 840 such that the camera opening 840 can hold and secure the second side camera 835. In such cases, the U-shaped socket 845 may also be turned over such that the open side of the U-shaped socket 845 may point at directions essentially pointed by the first side camera 827 and demonstrated by arrow 880.

Figure 9A:
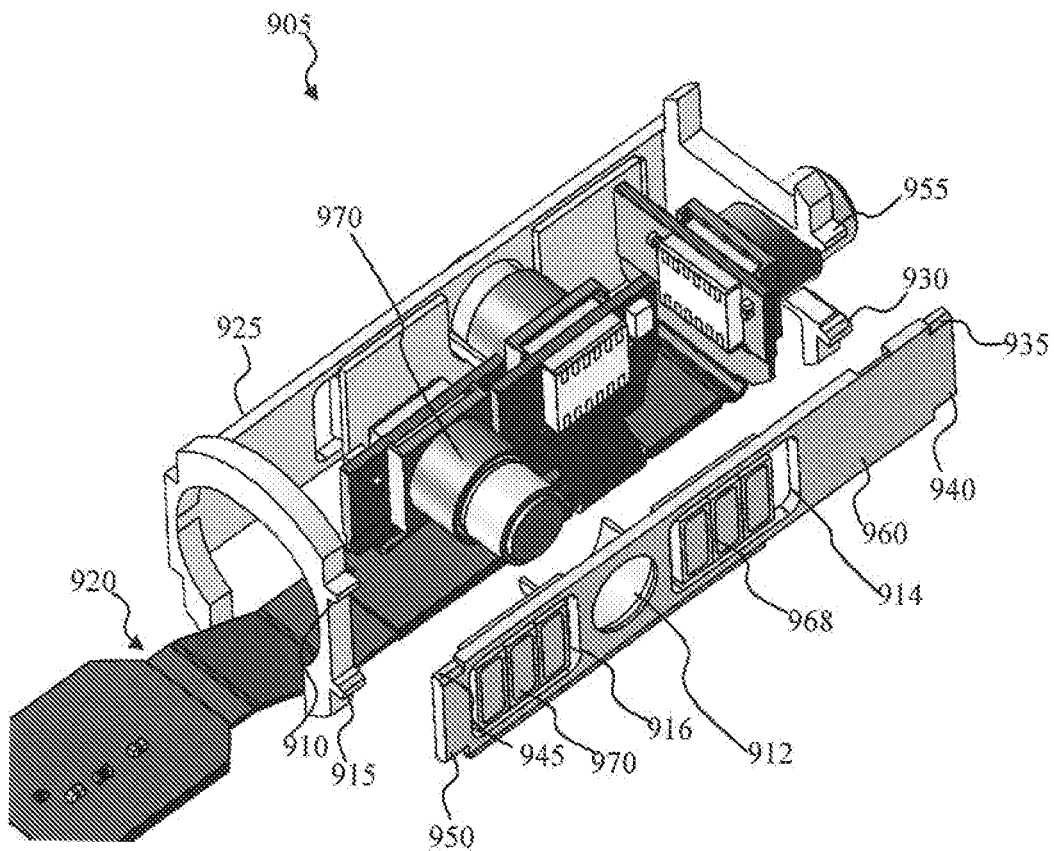
FIG. 9A shows a distal housing comprising a first component of a supporting cage mounted on a foldable circuit board in a folded position, and a second component of the supporting cage (in an exploded view)

FIG. 9A shows a distal housing comprising a first component of a supporting cage mounted on a foldable circuit board in a folded position, and a second component of the supporting cage in an exploded view, according to the disclosed subject matter. FIG. 9 shows a distal housing 905 comprising a first component of the supporting cage 925 mounted onto a foldable circuit board 920 and adapted to fasten, secure and hold the foldable circuit board 920 in a folded position. The distal housing 905 also comprises a second component of the supporting cage 960 adapted to hold, secure and support the foldable circuit board 920 in a folded position. The second component of the supporting cage 960 comprises a second side camera opening 912 and illuminator openings 914 and 916 placed on either side of second side camera opening 912. Second side illumination modules 968, and 970 can also be mounted onto the second component of the supporting cage 960, wherein the side illumination module 968 can fit into the illuminator opening 914, and wherein the side illumination module 970 can fit into the illuminator opening 916 or vice versa. Thus, illuminator opening 914, and 916 of second component of the supporting cage 960 may also hold and secure side illumination modules 968 and 970.

The first component of the supporting cage 925 further comprises rail shaped slots 910, 915, 955 and 930, which in some cases may be utilized to piece together the first component of the supporting cage 925 and the second component of the supporting cage 960. Thus, the second component of the supporting cage 960 may comprise protuberant edges 945, 950, 935, and 940 which can fit into the slots/grooves 910, 915, 955 and 930, respectively. In some cases, the protuberant edges 945, 950, 935 and 940 may be rounded or quadrilateral.

Yet in some other possible embodiments, first component of supporting cage 925 may have protuberant edges adapted to align with slots/grooves within second component of supporting cage 960. Thus, the rail shaped slots 910, 915, 955 and 930 of the first component of the supporting cage 925 may be replaced by protuberant edges and the protuberant edges 945, 950, 935, and 940 may be replaced by rail shaped slots, which in some cases may be utilized to piece together the first component of the supporting cage 925 with the second component of the supporting cage 960. Thus, the second component of the supporting cage 960 may comprise rail shaped slots 945, 950, 935, and 940 which can fit into the protuberant edges 910, 915, 955 and 930, respectively. In some case, the protuberant edges may be rounded or quadrilateral.

Figure 9B:
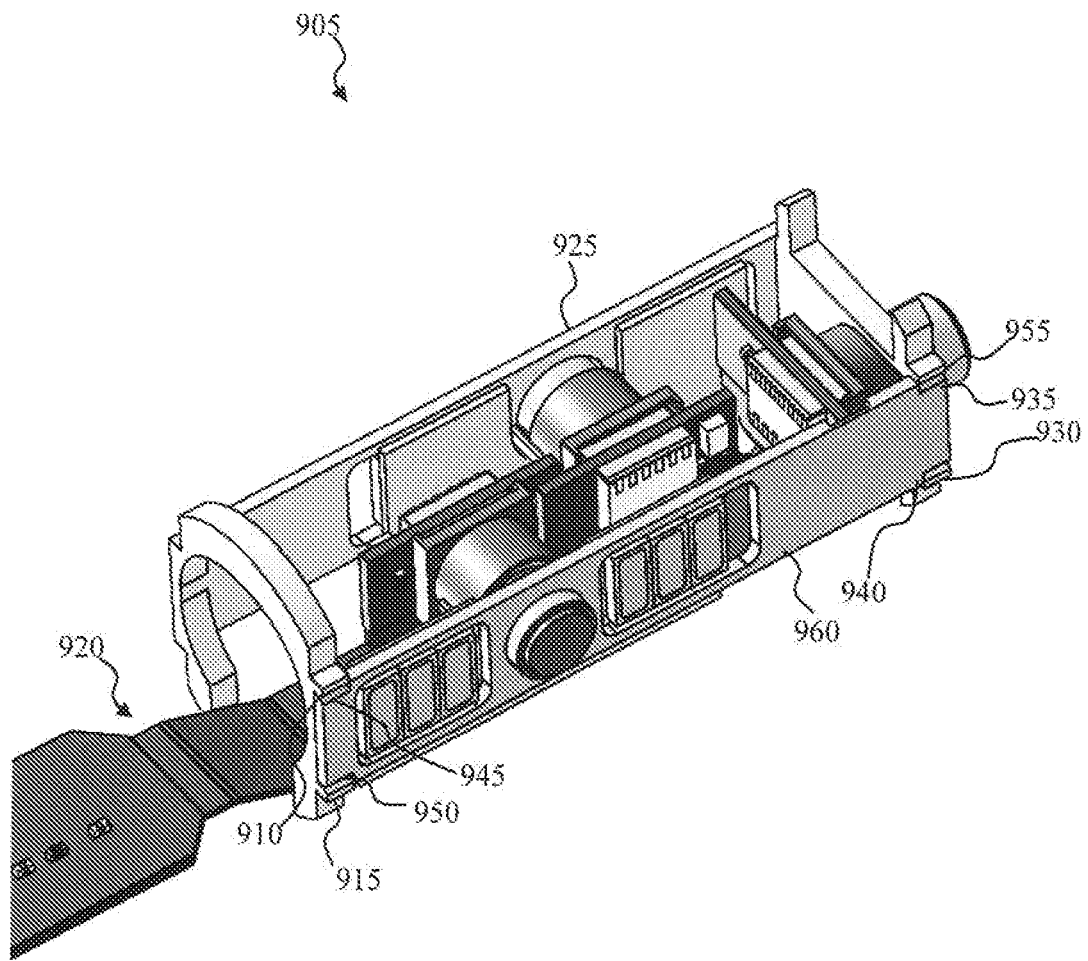
FIG. 9B shows a distal housing comprising a first component of a supporting cage mounted onto a foldable circuit board in a folded position, and a second component of the supporting cage connected to the first component of a supporting cage, according to FIG. 9A.

FIG. 9B shows a distal housing comprising a first component of a supporting cage mounted onto a foldable circuit board in a folded position, and a second component of the supporting cage connected to the first component of a supporting cage, according to FIG. 9A. FIG. 9B shows a distal housing 905 comprising a first component of the supporting cage 925 mounted on a foldable circuit board 920, and a second component of the supporting cage 960 piece together with the first component of the supporting cage 925.

In some cases, the first component of the supporting cage 925 can be connected to the second component of the supporting cage 960, wherein the pointed/protuberant edge 945 is inserted into the slot/groove 910, the protuberant edge 950 is inserted into the slot/groove 915, protuberant edge 935 is inserted into the slot/groove 955, and the protuberant edge 940 is inserted into the slot/groove 930.

Figure 10A:
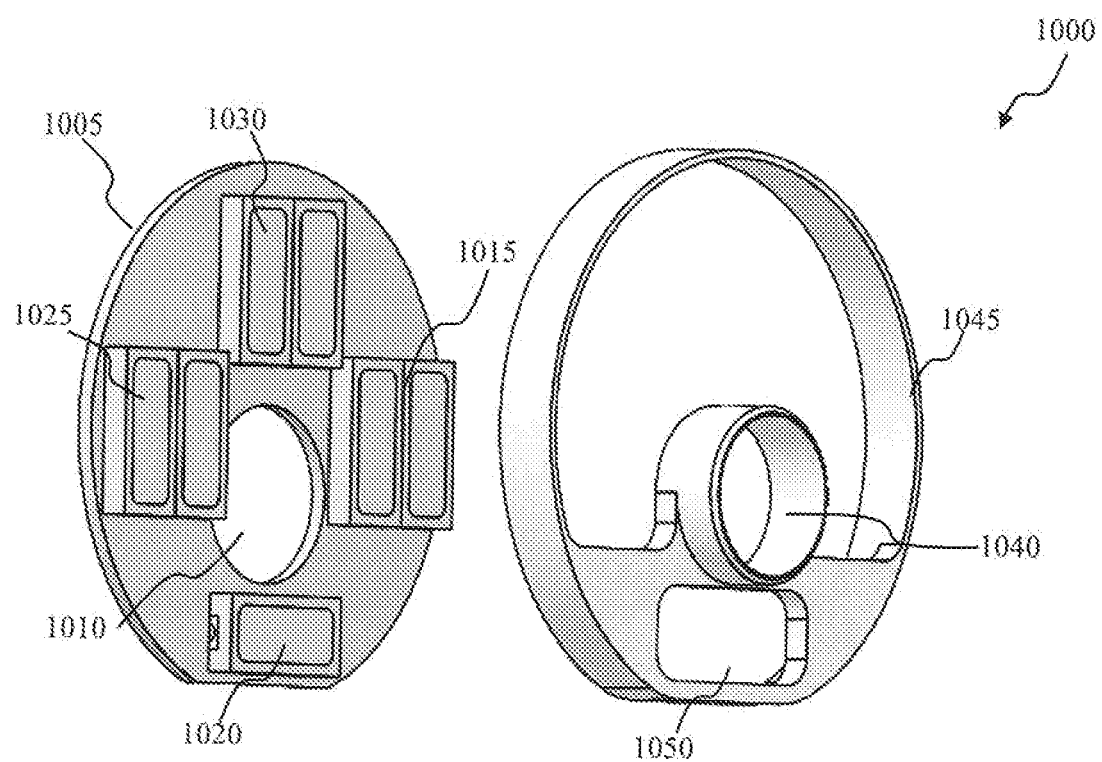
FIG. 10A shows a front illumination unit of a medical imaging device, in an exploded view, according to exemplary embodiments of the disclosed subject matter.

FIG. 10A shows a front illumination unit of a medical imaging device, in an exploded view, according to exemplary embodiments of the disclosed subject matter. FIG. 10A shows a front illumination unit 1000 having a front illuminator electronic circuit 1005 which can hold a set of one or more illumination modules, for example four front illumination modules, 1015, 1020, 1025, and 1030. The front illuminator electronic circuit 1005 also comprises a round aperture 1010 adapted to allow the front lens of the front camera (not shown) to insert therein. FIG. 10A also shows a front round frame 1045 for supporting the front illuminator electronic circuit 1005 within the front round frame 1045. The front round frame 1045 may also comprise a front camera supporting aperture 1040 for supporting and securing the front camera (not shown) which may be located within the front round frame 1045. The front round frame 1045 may also comprise an aperture 1050 for supporting illumination module, for example the illumination module 1025, within the front round frame 1045.

In some embodiments of the disclosed subject matter, the front camera supporting aperture 1040 may be located at the center of the front round frame 1045, such that the center of the aperture 1040 may be essentially at the center of the front round frame 1045. In some possible embodiments of the disclosed subject matter, the center of the aperture 1040 may be situated away from the center of the front round frame 1045.

Figure 10B:
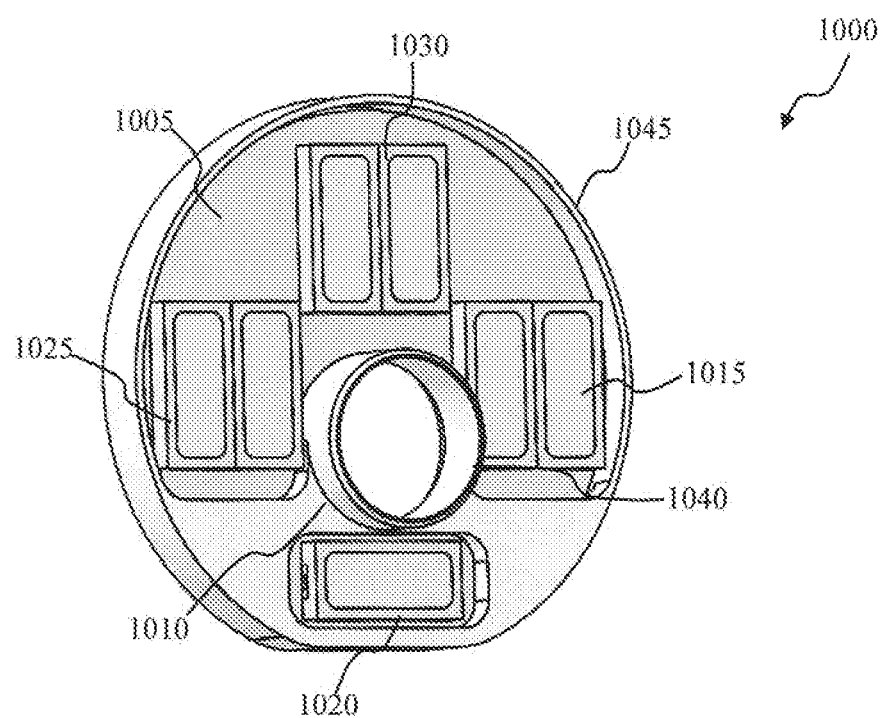
FIG. 10B shows a front illumination unit of a medical imaging device, according to FIG. 10A.

FIG. 10B shows a front illumination unit of a medical imaging device, according to FIG. 10A. FIG. 10B shows a front illumination unit 1000 which may include a front illuminator electronic circuit 1005 which can hold a set of one or more illumination modules, for example four front illumination modules, 1015, 1020, 1025, and 1030. The front illuminator electronic circuit 1005 also comprises a round aperture 1010 adapted to allow the front lens of the front camera (not shown) to insert in. The front illuminator electronic circuit 1005 can be inserted into the front round frame 1045 for supporting thereof. The front round frame 1045 may also comprise a front camera supporting aperture 1040 for supporting and securing front camera (not shown) located within the front round frame 1045. Thus, the front illumination modules 1015, 1020, 1025, and 1030 may hold a different number of illuminators. In some embodiments, front illuminator electronic circuit 605 can hold a set of 1, 2, 3, 4, 5 or more front illumination modules.

FIGS. 11A-11B show a distal tip of a medical imaging device with a multi camera rigid cover, a front camera and a front round frame, according to the disclosed subject matter. FIG. 11A shows an exploded view of distal tip 1100 comprising a multi camera rigid cover 1105. The distal tip 1100 also comprises a distal housing with a front camera 1115. FIG. 11A also shows a front frame 1125 shaped to fit into the multi camera rigid cover 1105 and thereby hold and secure the front camera 1115. FIG. 11B shows front frame 1125 inserted into the multi camera rigid cover 1110 for holding and securing the front camera 1120 therein.

Figure 12:
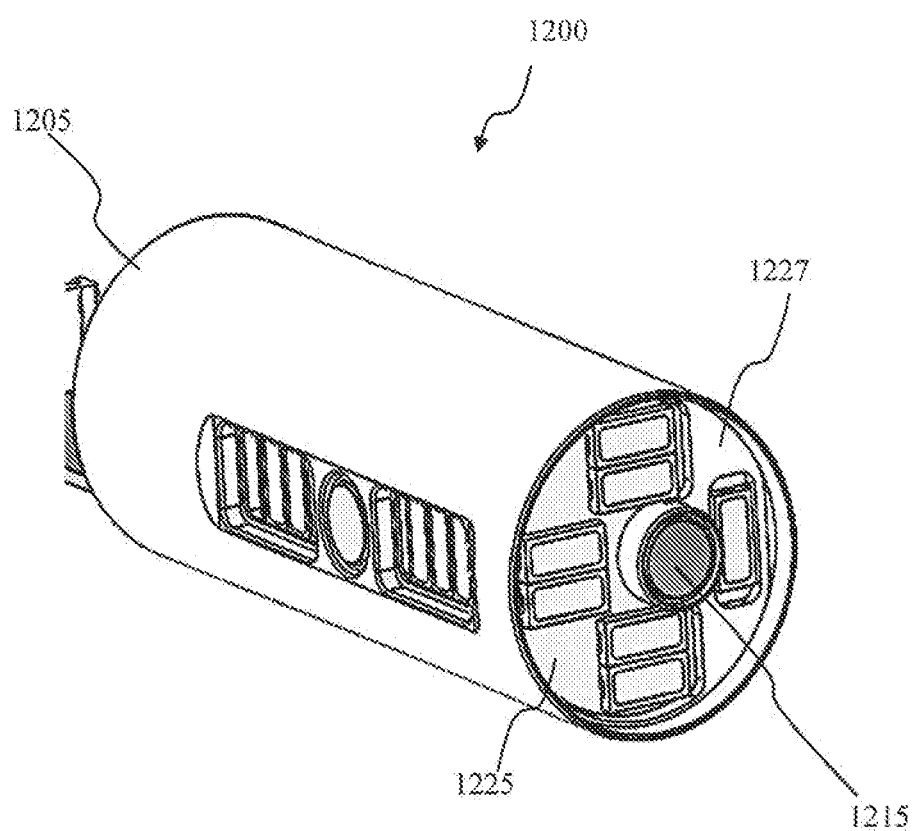
FIG. 12 shows a distal tip of a medical imaging device comprising a multi camera rigid cover, a distal housing, a front frame, a front optical window, and a front illuminator electronic circuit, according to the disclosed subject matter.

FIG. 12 shows a distal tip of a medical imaging device comprising a multi camera rigid cover, a distal housing, a front frame, a front optical window, and a front illuminator electronic circuit, according to the disclosed subject matter. FIG. 12 shows a view of a distal tip 1200 comprising a multi camera rigid cover 1205. The distal tip 1200 also comprises a distal housing with a front camera 1215. Distal tip 1200 further comprises a front illuminator electronic circuit 1225 and a front frame 1227. In some cases, the front illuminator electronic circuit 1225 may be inserted into the multi camera rigid cover 1205 first, followed by the front frame 1227, to situated on the top of the front illuminator electronic circuit 1225, such front frame 1227 may hold, secure and support and front illuminator electronic circuit 1225 within distal tip 1200.

Figure 13:
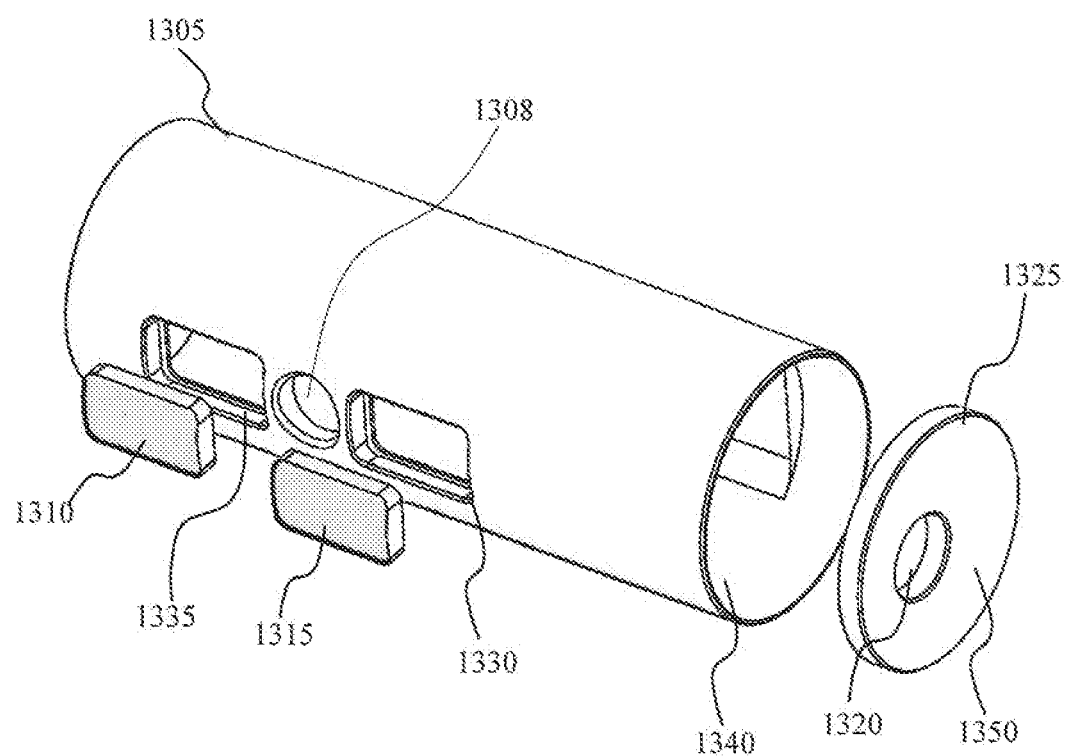
FIG. 13 illustrates an exploded view of a multi camera rigid cover with illuminator optical windows, according to the disclosed subject matter.

FIG. 13 illustrates an exploded view of a multi camera rigid cover with illuminator optical windows, according to the disclosed subject matter. FIG. 13 shows a multi camera rigid cover 1305 with side illuminator optical windows 1310, and 1315 and front illuminator optical window 1325. The front optical window 1325 comprises a camera aperture 1320 and designed to be inserted within a front opening 1340 of the multi camera rigid cover 1305. FIG. 13 also shows a side illuminator optical window 1310 which can be inserted into the illuminator opening 1335, and a side illuminator optical window 1315 which can be inserted into the illuminator opening 1330. A side camera aperture 1308 is located between side illuminator optical window 1310 and side illuminator optical window 1315 within the multi cover rigid cover 1305 lateral surface. Typically, side camera aperture 1308 and side illuminator optical windows 1310 and 1315 are aligned along a longitudinal axis of the multi cover rigid cover 1305. Side camera aperture 1308 configured to hold, support and secure a side camera (not shown). In some cases, the front illuminator optical window 1325, the side illuminator optical window 1310, and the side illuminator optical window 1315 may comprise a transparent material such as glass or plastic in order to allow the light enlighten through the optical windows. For example, the front surface 1350 may comprise transparent material such as glass or plastic which allow the light emitted by the illumination modules to spread out to the outer space of the multi camera rigid cover 1305.

In some cases, the front illuminator optical window 1325, the side illuminator optical window 1310, and the side illuminator optical window 1315 may be connected to the front opening 1340, the illuminator opening 1335, and to illuminator opening 1330 by adhesive material, screws, clamping devices, and the like. In some embodiments, front illuminator optical window 1325, side illuminator optical windows 1310 and 1315 may be attached front opening 1340 and illuminator openings 1335 and 1330 in replaceable manner techniques, this enables the replacement of illuminator modules or any illuminator within these modules (not shown).

In accordance with an embodiment of the present specification, multi camera rigid cover 1305 may house the internal optic and electronic components of the distal tip of the rigid scope. Tip cover may be configured to fit over the distal housing of the distal tip, including the optical gear of front and at least one side optical gears and associate illuminator optical windows, and to provide protection to the internal components. Illuminator optical windows 1310, 1330 and 1325 are respectively aligned with the corresponding opening 1335, 1330 and 1340 within multi camera rigid cover 1305, such provide sealing and protection to the illuminator modules.

Figure 14:
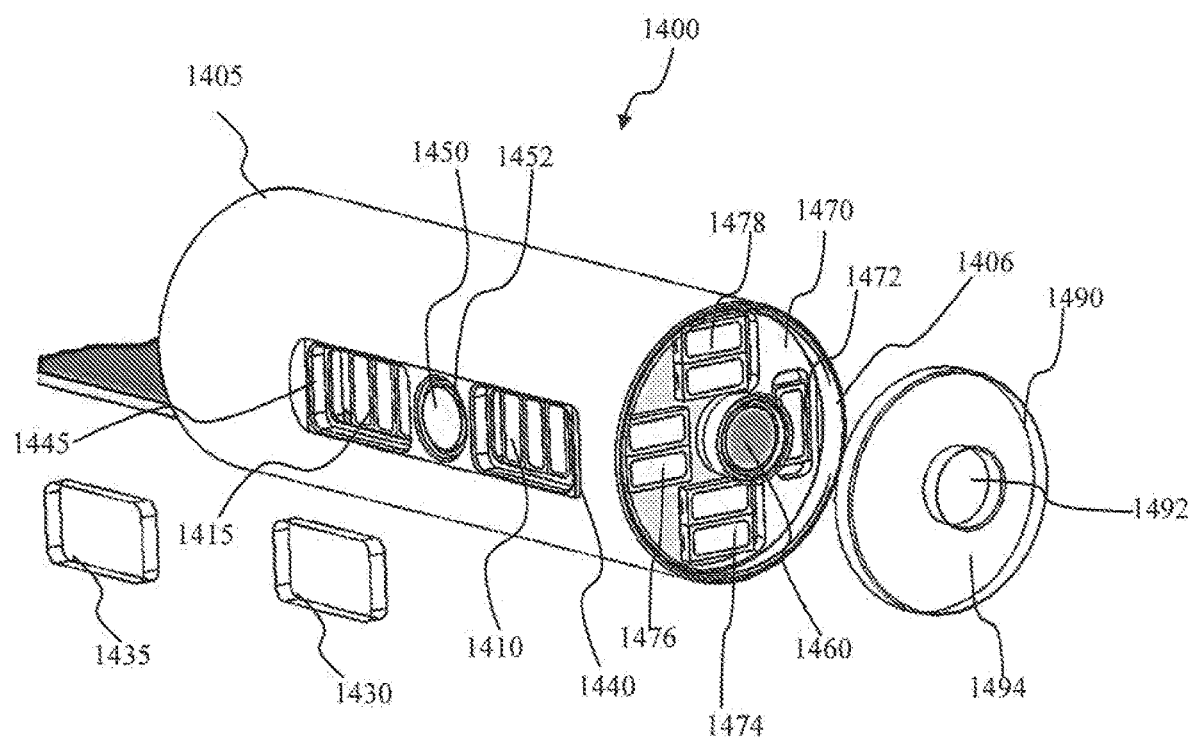
FIG. 14 illustrates an exploded view of a distal tip of a medical imaging device and a multi camera rigid cover with illuminator optical windows, according to FIG. 12 and FIG. 13, respectively.

FIG. 14 illustrates an exploded view of a distal tip of a medical imaging device and a multi camera rigid cover with illuminator optical windows, according to FIG. 12 and FIG. 13, respectively. FIG. 14 shows a view of a distal tip 1400 comprising a multi camera rigid cover 1405 configured to cover a distal housing and a front optical gear. The multi camera rigid cover 1405 may comprise illuminators openings 1440, and 1445 adapted to hold, secure and support side optical windows 1430, and 1435 .... The side optical windows 1430 and 1435 may be configured to allow access to the illumination modules 1410, and 1415 of the distal tip 1400 without removing the multi camera rigid cover 1405. In some embodiments, side illuminator optical windows 1430 and 1435 may be attached to illuminator openings 1440 and 1445 in replaceable manner techniques, which enable the replacement of illuminator modules 1410 and 1415 or any illuminator within these modules.

The multi camera rigid cover 1405 also comprise a distal opening 1406 configured to hold, secure and support a front optical window 1490 having a front camera aperture. The front optical windows 1490 has a transparent surface 1494 which may allow the light of front illumination modules 1472, 1474, 1476, and 1478 to enlighten to the outer space of the multi camera rigid cover 1405. In some cases, the front optical windows 1490 may be configured to allow access to the front illumination modules 1472, 1474, 1476, and 1478. Front optical windows 1490 may be attached to distal opening 1406 of multi camera rigid cover 1405 in replaceable manner techniques, this enables the replacement of illuminator modules 1472, 1474, 1476, and 1478 or any illuminator within these modules.

In another embodiment, the number and location of front illuminators may vary for example, less than 4 set of illuminators or more wherein each set of illuminators has 1, 2, 3, 4 or more LED and may emit the same light spectrum or different light spectrum.

While the disclosure has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this invention, but only by the claims that follow.

The invention claimed is:
1. A medical imaging device, comprising:
a rigid elongated member,
a rigid distal member connected to the rigid elongated member, wherein said distal member comprises a front camera, a first side camera and a second side camera;
a foldable circuit board located within the rigid distal member, said foldable circuit board comprises a front foldable arm connected to said front camera, a first side foldable arm connected to said first side camera and a second side foldable arm connected to said second side camera;
wherein said foldable circuit board is designed to be put in a foldable position and inserted into said distal member;

a base of the second side foldable arm is positioned further from the front foldable arm than a base of the first side foldable arm is from the front foldable arm.

2. The medical imaging device of claim 1, wherein the front foldable arm, the first side foldable arm, and the second side foldable arm have an open position in which the foldable arms are substantially parallel to the surface of the main rigid section and a folded position in which the foldable arms form an angle versus the surface of the main rigid section.

3. The medical imaging device of claim 1, wherein the foldable arm associated with the first side camera and the foldable arm associated with the second side camera overlap on an axis parallel to the longitudinal axis of the rigid distal member.

4. The medical imaging device of claim 1, wherein the rigid distal member further comprises a cage designed to be mounted onto said foldable circuit board.

5. The medical imaging device of claim 4, wherein the cage is designed to be mounted onto said foldable circuit board wherein the foldable circuit board is in a folded position.

6. The medical imaging device of claim 4, wherein the cage comprises a longitudinal bar having multiple apertures configured to secure the front camera, the first side camera and the second side camera.

7. The medical imaging device of claim 4, the cage further comprises a U-shaped closure configured to support and hold electronic cables within the cage and thereby limits movement of the foldable circuit board within the distal member.

8. The medical imaging device of claim 1, wherein the rigid distal member further comprises a front illumination unit for illuminating the area captured by the front camera and a lateral illumination unit for illuminating the area captured by the first side camera, wherein the front illumination unit comprises four illumination modules.

9. The medical imaging device of claim 1, wherein the rigid distal member further comprises one or more side illumination electric circuits and illumination modules, a front optical window located at the front of said rigid distal member, and at least one side optical window located at the lateral surface of said distal member adapted to seal and cover the one or more side illumination electric circuits and illumination modules.

10. The medical imaging device of claim 1, wherein the foldable circuit board comprises conductors and electronic cables and further comprises a rear rigid section adapted to carry at least some of the conductors and electronic cables of the foldable circuit board, such that the rear rigid section extends from a distal tip into a rigid shaft of the medical imaging device.

* * * * *